United States Patent [19]

Henderson et al.

[11] 4,340,730

[45] Jul. 20, 1982

[54] N[6]-SUBSTITUTED ADENOSINES

[75] Inventors: Richard E. L. Henderson, Evanston; Nancy J. Malek, Skokie; Alan E. Moormann, Skokie; Barnett S. Pitzele, Skokie, all of Ill.

[73] Assignee: G. D. Searle & Co., Skokie, Ill.

[21] Appl. No.: 229,824

[22] Filed: Jan. 30, 1981

Related U.S. Application Data

[63] Continuation-in-part of Ser. No. 157,625, Jun. 9, 1980, abandoned.

[51] Int. Cl.$^3$ ............................................. C07H 19/16
[52] U.S. Cl. ........................................ 536/26; 536/24
[58] Field of Search ...................... 536/24, 26, 27, 28

[56] References Cited

U.S. PATENT DOCUMENTS 3,983,104 9/1976 Vorbruggen .......................... 536/24

OTHER PUBLICATIONS

Chemical Abstracts, vol. 89, p. 698, Abst. No. 44080t, 1971.
Chemical Abstracts, vol. 84, p. 579, Abst. No. 150915a, 1976.
Chemical Abstracts, vol. 78, p. 418, Abst. No. 136628d, 1973.
Chemical Abstracts, vol. 74, p. 503, Abst. No. 126022l, 1971.
Current Abstracts of Chemistry, vol. 40, Iss. 402, Abstract No. 203138, 1973.
Current Abstracts of Chemistry, vol. 53, Iss. 550, Abstract No. 218025, 1974.
Current Abstracts of Chemistry, vol. 59, Iss. 618, Abstract No. 234711, 1975.
Current Abstracts of Chemistry, vol. 31, Iss. 265, Abstract No. 105094, 1968.
Current Abstracts of Chemistry, vol. 58, Iss. 605, Abstract No. 231440, 1975.
Current Abstracts of Chemistry, vol. 53, Iss. 552, Abstract No. 218616, 1974.
Current Abstracts of Chemistry, vol. 31, Iss. 264, Abstract No. 104601, 1968.
Current Abstracts of Chemistry, vol. 33, Iss. 282, Abstract No. 110595, 1969.
Current Abstracts of Chemistry, vol. 71, Iss. 781, Abstract No. 228974, 1978.
Current Abstracts of Chemistry, vol. 57, Iss. 594, Abstract No. 228702, 1975.
Current Abstracts of Chemistry, vol. 71, Iss. 781, Abstract No. 272442, 1978.
Derwent Abstracts, 36435, NE 68, 12083, 1967.
Derwent Abstracts, 100, Brit. 863715, 1957.
Derwent Abstracts, 35637, NE 68, 08783, 1967.
Derwent Abstracts, 21149T, JA 085409, 1969.
Derwent Abstracts, 60425W/37, BE 828259, 1974.
Derwent Abstracts, 75775T-B, JA 026092, 1970.
Derwent Abstracts, 7857, US. 3,092632, 1960.
Derwent Abstracts, 21907, Jap 10/15/66, 1963.
Derwent Abstracts, 12142, S.Ab. 63/5224, 1963.
Derwent Abstracts, 33288, BE 709,014, 1967.
Derwent Abstracts, 75776T-B, Ja. 26093, 1972.
Derwent Abstracts, 20744X/12, GB 038278, 1976.

*Primary Examiner*—Blondel Hazel
*Attorney, Agent, or Firm*—James G. Passe; W. Dennis Drehkoff

[57] ABSTRACT

Novel N[6]-adenosines according to formula I are disclosed. These novel compounds are useful as antihypertensive agents.

16 Claims, No Drawings

N⁶-SUBSTITUTED ADENOSINES

This application is a continuation-in-part of application Ser. No. 157,625 filed June 9, 1980, now abandoned.

BACKGROUND OF THE INVENTION

Since the etiology of most cases of hypertension is unknown, the search for effective antihypertensive agents is largely empirical, and various classes of agents are currently employed to treat hypertensive patients.

The search for improved agents has continued because of the significant, adverse side-effects produced by all effective antihypertensive agents, and because of the not infrequent need to periodically change or modify therapy.

N⁶-substitution of adenosine has produced compounds having widely varying activities, i.e., coronary dilating and blood platelet aggregation inhibitory activities, antihypercholesteremic, anti-tumor, anti-viral, growth-promoting activity and anti-hypertensive activities.

The present invention provides N⁶-substituted adenosines which are useful as antihypertensive agents. This is surprising because of the widely varying and unpredictable utilities of the N⁶-substituted adenosines.

SUMMARY

The present invention provides N⁶-adenosines which are useful as antihypertensive agents. The compounds of this invention are represented by formula 1 on Chart A. The present invention particularly provides:

A compound according to formula 1
wherein $R_1$ is:
  (a) hydrogen; or
  (b) alkyl of from 1 to 6 carbon atoms inclusive;
wherein $R_2$ is:
  (a) hydrogen;
  (b) 2-methylimidazol-5-ylmethyl-thio) ethyl;
  (c) 2-(heptamethyleneiminyl)ethyl;
  (d) 4-(N,N-dimethylaminophenethyl);
  (e) —$(CH_2)_n COOR_5$;
wherein n is an integer from 3 to 11 inclusive;
wherein $R_5$ is:
  (a) hydrogen; or
  (b) alkyl of from 1 to 20 carbon atoms inclusive;
    with the proviso that when $R_1$ is hydrogen and n is 5, $R_5$ cannot be hydrogen;
  (f) 3(10,11-dihydro-5H-dibenz[b,f]azepin-5-yl) propyl
  or wherein $R_1$ and $R_2$ taken together with N from a piperazine ring of formula II;
wherein $R_4$ is:
  (a) ethoxycarbonyl; or
  (b) alkyl of 1 to 6 carbon atoms inclusive;
  and the pharmaceutically acceptable salts thereof.

Alkyl of from 1 to 6 carbon atoms inclusive refers to straight or branched chain alkyl radicals having from 1 to 6 carbon atoms e.g., methyl, ethyl, propyl, butyl, pentyl, hexyl and branched chain isomers thereof.

The term "pharmaceutically acceptable salts" refers to non-toxic acid addition salts of the compounds of this invention which are generally prepared by reacting the free base with a suitable organic or inorganic acid. Representative salts include the hydrochloride, hydrobromide, sulfate, bisulfate, acetate, oxalate, valerate, oleate, palmitate, stearate, laurate, borate, benzoate, lactate, phosphate, tosylate, citrate, maleate, fumarate, succinate, tartrate, napsylate and the like salts.

DESCRIPTION OF PREFERRED EMBODIMENTS

The compounds of this invention are useful as antihypertensive agents when administered orally or parenterally at dosages of from 1.5 to 100 mg/kg daily to hypertensive patients, preferably in divided doses.

Generally speaking, the compounds of this invention can be prepared by reacting 6-chloropurine riboside, formula XI of Chart B, with an appropriate amine in the presence of a base in water or alcohol, $R_3OH$, where $R_3$ may or may not be the same as $R_2$, at reflux, according to the reaction scheme on Chart B.

The compounds of this invention can be administered either by oral or parenteral routes of administration. In the case of oral administration, the compounds are administered in daily dosages of from 15 to 100 mg/kg, preferably from 20 to 50 mg/kg depending upon the individual patient's response. In the case of parenteral administration, e.g., intravenous, intramuscular, intraperitoneal or subcutaneous routes, the esters and acids are administered at dosages of from 1.5 to 50 and preferably from 5 to 20 mg/kg daily to hypertensive, mammalian patients.

The omega-amino esters are prepared by one of two general methods. For esters of more volatile alcohols (e.g., those boiling at less than 200° C.), thionyl chloride is added to cold (ice bath) alcohol in an inert, dry atmosphere and the appropriate amino acid is added thereto. After heating at reflux, the solution is concentrated to dryness and triturated with diethyl ether to provide the omega-amino acid esters as hydrochlorides.

The second method, employed for esters of less volatile alcohols, entails heating the amino acid and appropriate alcohol at reflux in toluene with an excess of p-toluenesulfonic acid (pTsOH), using a Dean-Stark trap to remove water. The omega-amino ester precipitates as the tosylate salt upon cooling.

The following examples further illustrate the present invention.

EXAMPLE 1

Preparation of N⁶-(4-carboxybutyl)adenosine

A mixture of 15.0 g (52.3 mmole) of 6-chloropurine riboside, 15.2 g (130 mmole) of 5-aminopentanoic acid, and 11.1 g (59.9 mmole) of tributylamine in 450 ml of 90% aqueous n-propanol was heated at reflux for two days. The solution was cooled to approximately 0° C., and a first crop of crude product (9.1 g) was collected. An additional crop of 4.8 g was collected by concentrating the filtrate to approximately half of the original volume. A solution of the combined solids in hot aqueous ethanol was filtered and concentrated by boiling to remove most of the ethanol, leaving approximately 75 ml of aqueous solution. Upon cooling, the solution produced a fluffy, white precipitate which has collected, washed with water and dried to yield 12.9 g (35.1 mmole) of N⁶-(4-carboxybutyl)adenosine:

Analysis Calculated for $C_{15}H_{21}N_5O_6$: C, 49.04; H, 5.76; N, 19.06. Found: C, 48.79; H, 5.81; N, 18.66.

The NMR spectrum confirmed the structure.

EXAMPLE 2

Preparation of $N^6$-[4-(ethoxycarbonyl)butyl]adenosine

A mixture of 10.0 g (34.9 mmole) of 6-chloropurine riboside, 9.5 g (52.3 mmole) of ethyl-5-aminopentanoate hydrochloride (prepared by the method of Example 7), and 18.0 g (97.1 mmole) of tributylamine in 200 ml of absolute ethanol was heated at reflux for 18 hours, then allowed to cool to about 0° C. The resulting crude product was collected and washed with ethanol, redissolved in 100 ml of boiling ethanol and filtered. Upon cooling, two crops of $N^6$-[4-(ethoxycarbonyl)butyl]adenosine totalling 7.9 g (20.0 mmole) were collected as a fluffy white powder.

Anal. Calcd for $C_{17}H_{25}N_5O_6$: C, 51.64; H, 6.37; N, 17.71. Found: C, 51.41; H, 6.45; N, 17.68.

The NMR spectrum confirmed the identity of the product.

EXAMPLE 3

Preparation of $N^6$-methyl-$N^6$-(3-carboxypropyl)adenosine

A mixture of 10.0 g (34.9 mmole) of 6-chloropurine riboside, 11.0 g (71.6 mmole) of 4-(methylamino)butanoic acid hydrochloride, and 20.0 g (108 mmole) of tributylamine in 300 ml of propanol was heated at reflux for two days. The solution was allowed to cool and concentrated in vacuo to a thick oil. The oil was treated with several portions of diethyl ether to remove soluble organic material. Two crops of crude product were crystallized from ethanol and redissolved in 100 ml of 50% aqueous ethanol. The resulting solution was decolorized with charcoal, filtered, and the volume was reduced to about 30 ml by boiling. Upon cooling, 4.3 g (11.7) mmole) of $N^6$-methyl-$N^6$-(3-carboxypropyl)adenosine was obtained as a fluffy white solid.

Anal. Calcd. for $C_{15}H_{21}N_5O_6$: C, 49.04; H, 5.76; N, 19.06. Found: C, 48.91; H, 5.83; N, 18.67.

The NMR spectrum confirmed the identity of the product.

EXAMPLE 4

Preparation of $N^6$-methyl-$N^6$-[3-(ethoxycarbonyl)propyl]adenosine

A mixture of 7.0 gm (24.4 mmole) of 6-chloropurine riboside, 6.0 gm (33.0 mmole) of ethyl 4-(methylamino) butanoate hydrochloride, and 6.0 gm (59.3 mmole) of triethylamine in 200 ml of absolute ethanol was heated at reflux for four days. Upon cooling, the mixture gave a first crop of crude product; concentration of the filtrate gave a second crop. The combined solids were purified by column chromatography using silica gel packed and eluted with acetone. Subsequent recrystallization from ethanol yielded 4.9 gm (12.4 mmole) of $N^6$-methyl-$N^6$-[3-(ethoxycarbonyl)propyl]adenosine as a fluffy white solid.

Anal. Calcd. for $C_{17}H_{25}N_5O_6$: C, 51.64; H, 6.37; N, 17.71. Found: C, 51.69; H, 6.41; N, 17.40.

The NMR spectrum confirmed the identity of the product.

EXAMPLE 5

Preparation of ethyl 5-aminopentanoate hydrochloride

To 100 ml of absolute ethanol, stirred under a dry nitrogen atmosphere and cooled in an ice bath, was added 12.0 ml (167 mmole) of thionyl chloride, followed by 10.0 gm (85.3 mmole) of 5-aminopentanoic acid. The mixture was heated at reflux for 18 hours, cooled and concentrated in vacuo to a sticky solid. The crude ester was triturated with 150 ml of diethyl ether, and the resultant fluffy white solid was collected, washed thoroughly with diethyl ether, and dried in vacuo over potassium hydroxide to give 14.3 gm (78.7 mmole) of ethyl 5-aminopentanoate hydrochloride. The ester was sufficiently pure according to nmr spectroscopy (in $(CD_3)_2SO$) for subsequent use without further purification.

EXAMPLE 6

Preparation of n-octadecyl 5-aminopentanoate, tosylate salt

A mixture of 5.05 gm (43.1 mmole) of 5-aminopentanoic acid, 23.3 gm (86.1 mmole) of stearyl alcohol, and 12.0 gm (63.1 mmole) of p-toluenesulfonic acid monohydrate in 200 ml of toluene was heated at reflux, using a Dean-Stark trap to remove water. After 90 minutes, the solution was allowed to cool to 0° C., giving a heavy gelatinous precipitate. The crude ester was collected, washed thoroughly with toluene, triturated with diethyl ether, and dried in vacuo to give 21.1 gm (38.8 mmole) of fluffy white octadecyl 5-aminopentanoate as the tosylate salt. The ester was sufficiently pure according to nmr spectroscopy (in $(CD_3)_2SO$) for subsequent use without further purification.

EXAMPLE 7

Preparation of 5-(methylamino)pentanoic acid hydrochloride

A mixture of 75 gm (0.66 mmole) of 1-methyl-2-piperidinone and 300 ml of 6 N hydrochloric acid was heated at reflux for 5.5 hours. The solution was then concentrated by distillation to about 70 ml, allowed to cool, and concentrated to dryness in vacuo. The resultant white solid, upon thorough drying, gave a quantitative yield of analytically pure 5-(methylamino)pentanoic acid hydrochloride.

Anal. Calcd. for $C_6H_{14}N O_2Cl$: C, 42.99; H, 8.42; N, 8.36; Cl, 21.15. Found: C, 42.72; H, 8.47; N, 8.34; Cl, 21.18.

In the examples 8 and 9 the reactions are followed by TLC using a methanol/methylene chloride solvent system with a constant 0.1% ammonium hydroxide system. The ratio of methanol to methylene chloride is dependent on the polarity of the starting materials and products. Reactions are refluxed until there is no change in the TLC of the previous check.

EXAMPLE 8

$N^6$-[2-(4-methylimidazol-5-ylmethylthio)ethyl]adenosine(formula I of Chart A: $R_1$ is hydrogen, and $R_2$ is 4-Methyl-5-[(2-aminomethyl)-thiomethyl]-imidazole)

5.0 g of 6-chloropurine riboside (0.0179 moles) 4.6 g of 4-methyl-5-[(2 aminoethyl)-thiomethyl]-imidazole (0.019 moles), and 8.78 ml of triethylamine (0.063 moles) are refluxed overnight in 100 ml of ethanol. 15 ml of solvent are then removed with nitrogen gas. The crystals formed therefrom are filtered and washed with ethanol. The crystals are then recrystallized from ethanol and washed with diethyl ether.

Anal. Calcd. for $C_{17}H_{22}N_7O_4S$ ¼$H_2O$: C, 48.04; H, 5.34; N, 23.07; S, 7.54. Found: C, 48.31; H, 5.73; N, 22.67; S, 7.38.

EXAMPLE 9

6-(4-ethyl-1-piperazinyl)purine riboside(formula I of Chart A: $R_1$ and $R_2$ are taken together with N to form a piperizine ring of formula II and $R_4$ is ethyl)

5.0 g of 6-chloropurine riboside (0.0174 moles), 2.28 of N-ethyl piperazine (0.020 moles) and 2.12 g triethylamine (0.021 moles) are refluxed in 100 ml of ethanol for 12 hours under nitrogen atmosphere. The solution is stripped of half the solvent and cooled to room temperature. Crystals form which are filtered and washed with ethanol to yield 4.6 gms.

Anal. Calcd. For $C_{16}H_{24}N_6O_4 \cdot \frac{1}{2}H_2O$: C, 51.46; H, 6.75; N, 22.51. Found: C, 51.70; H, 6.72; N, 22.12.

Structure was confirmed by NMR.

The compounds in examples 10 through 13 are chromatographed by dissolving the compound in ethanol (methanol for example 10) and adding an equivalent weight of silica gel and evaporating the ethanol or methanol under a nitrogen stream. The resulting residue is placed on a column and eluted with a methanol/methylene chloride and a constant 0.1% ammonium hydroxide system. The ratio of the methanol to methylene chloride is increased from a typical starting concentration of 1% to 5% methanol to methylene chloride to /0.1% ammonium hydroxide in increments of 2% to 5% based on the progress of the column as monitored by TLC.

EXAMPLE 10

6-[4-(ethoxycarbonyl)-1-piperazinyl]purine riboside(formula I of Chart A: $R_1$ and $R_2$ are taken together with N to form a piperazine ring of formula II; $R_4$ is ethoxycarbonyl)

5.0 g of 6-chloropurine riboside (0.0174 moles), 3.16 g of ethyl N-piperazine carboxylate (0.020 moles) and 2.12 g of triethylamine are refluxed in 100 ml of ethanol for 12 hours under a nitrogen atmosphere. The observed crystalline solid is filtered and washed with ethanol and suction dried to yield 6.5 g. The crystals are then chromatographed (30% methanol/$CH_2Cl_2$,1%$NH_4OH$) to yield 5.5 gm.

Anal. Calcd. For $C_{17}H_{24}N_6O_6$: C, 49.99; H, 5.92; N, 20.57. Found: C, 49.89; H, 5.93; N, 20.28.

Structure was confirmed by NMR.

EXAMPLE 11

$N^6$-[2-(heptamethyleneiminyl)ethyl]adenosine(formula I of Chart A $R_1$ is hydrogen: $R_2$ is 2-heptamethyleneiminyl ethyl).

5.0 g of 6-chloropurine riboside (0.0174 moles) and 3.26 gms of N-[2-(heptamethyleneiminyl) ethyl] amine (0.0209 moles) and 3.87 g (5 ml) of tributylamine are refluxed in 100 ml ethanol overnight under nitrogen atmosphere. The solvent is then evaporated with nitrogen gas, and the crude product is chromatographed, then crystallized from ethanol. The product is filtered and washed with diethyl ether and then suction dried, then dried at 100° C. for 1 hour. Yield was 4.1 g Anal. Calcd. For $C_{19}H_{30}N_6O_4 \cdot \frac{1}{2}H_2O$; C, 55.52; H, 7.48; N, 20.45. Found: C, 55.59; H, 7.54; N, 20.63.

EXAMPLE 12

$N^6$-[3-(10,11-dihydro-5H-dibenz[b,f] azepin-5yl) propyl]-$N^6$-methyladenosine. (Formula 1 of Chart A: $R_1$ is methyl: $R_2$ is 3(10,11-dihydro-5H-dibenz[b,f] azepin-5-yl)propyl)

4.6 g of 6-chloropurine ribose (0.0165 moles), 5.0 g of desipramine HCl(0.0165 moles) and 4.8 ml (0.034 moles) of triethylamine are refluxed in 100 ml of ethanol overnight. The crude product is chromatographed, and the purified solid product is suspended in diethyl ether and filtered, washed with diethyl ether and suction dried to yield 7.2 g.

Anal. Calcd. For $C_{28}H_{32}N_6O_4$: C, 65.10; H, 6.24; N, 16.27 Found: C, 65.01; H, 6.03; N, 16.73.

NMR confirmed the structure.

EXAMPLE 13

$N^6$-[4-(N,N-dimethylamino)phenethyl] adenosine (formula 1 Chart A: $R_1$ is hydrogen; $R_2$ is 4-(N,N-dimethylamino)phenethyl)

5.0 g of 6-chloropurine ribose (0.017 moles) 4.5 g of 4-(N,N-dimethylamino)phenethylamine (0.019 moles) and 8.7 ml of triethyl amine are refluxed in 100 ml of ethanol overnight. The solvent is removed and the product is purified by column chromatography. The product is crystallized from methanol and suction dried to yield 2.1 g.

Anal. Calcd. For $C_{20}H_{26}N_6O_4 \cdot H_2O$: C, 55.54; H, 6.52; N, 19.43. Found: C, 55.64; H, 6.13; N, 19.17.

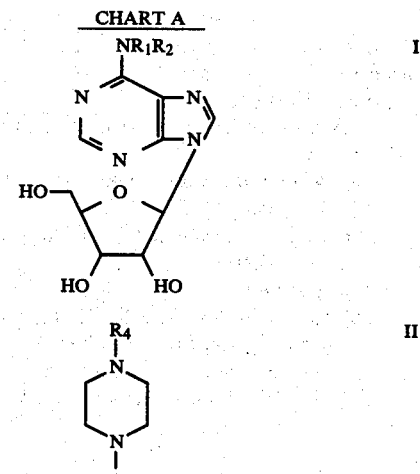

CHART A

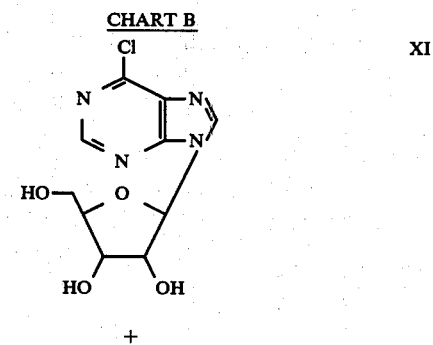

CHART B

-continued
CHART B $R_1NHR_2$

R$_3$OH at Reflux
Et$_3$N or Bu$_3$N

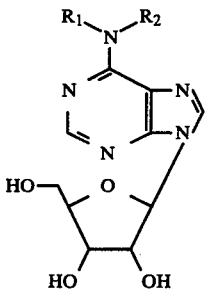

We claim:
1. A compound according to the formula:

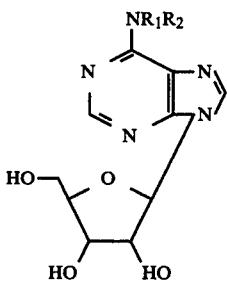

where in $R_1$ is:
(a) hydrogen; or
(b) alkyl of from 1 to 6 carbon atoms inclusive;
where $R_2$ is:
(a) 4-(N,N-dimethylaminophenethyl);
(b) —(CH$_2$)$_n$COOR$_5$;
   wherein n is an integer from 3 to 11 inclusive;
   wherein $R_5$ is:
   (a) hydrogen; or
   (b) alkyl of from 1 to 20 carbon atoms, inclusive with the provision that when $R_1$ is hydrogen and n is 5, $R_5$ cannot be hydrogen;
(c) 3(11,11-dihydro-5H-dibenz[b,f]azepin-5-yl)propyl;

or wherein $R_1$ and $R_2$ taken together with N form a piperazine ring of the formula:

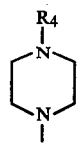

wherein $R_4$ is:
(a) ethoxycarbonyl.
2. A compound according to claim 1 wherein $R_1$ is hydrogen.
3. $N^6$-[4-(N,N-dimethylamino)phenethyl]adenosine a compound according to claim 2.
4. A compound according to claim 2 wherein $R_2$ is —(CH$_2$)$_n$COOR$_5$ and $R_5$ is alkyl of from 1 to 20 carbon atoms inclusive.
5. $N^6$-[4-ethoxycarbonyl)butyl]adenosine a compound according to claim 4.
6. A compound according to claim 2 wherein $R_2$ is —(CH$_2$)$_n$COOR$_5$ and $R_5$ is hydrogen, with the provision that when n is not equal to 5, then $R_1$ is not Hydrogen.
7. $N^6$-(4-carboxybutyl)adenosine a compound according to claim 6.
8. A compound according to claim 1 wherein $R_1$ is alkyl of from 1 to 6 carbon atoms inclusive.
9. A compound according to claim 8 wherein $R_1$ is methyl.
10. $N^6$-[3-(10,11-dihydro-5H-dibenz[b,f]azepin-5-yl)propyl]-$N^6$-methyladenosine a compound according to claim 9.
11. A compound according to claim 8 wherein $R_2$ is —(CH$_2$)$_n$COOR$_5$ and $R_5$ is hydrogen.
12. $N^6$-methyl-$N^6$-(3-carboxypropyl)adenosine a compound according to claim 11.
13. A compound according to claim 8 wherein $R_2$ is —(CH$_2$)$_n$ COOR$_5$ and $R_5$ is alkyl of 1 to 20 carbon atoms inclusive.
14. $N^6$-methyl-$N^6$-[3-ethoxycarbonyl)propyl]adenosine a compound according to claim 13.
15. A compound according to claim 1 wherein $R_1$ and $R_2$ taken together with N form a piperazine ring of formula II.
16. 6-[4-ethoxycarbonyl)-1-piperazinyl]purine riboside, a compound according to claim 15.

* * * * *